United States Patent
Biermann et al.

[11] Patent Number: 6,005,909
[45] Date of Patent: Dec. 21, 1999

[54] METHOD OF CONTROLLING A TOMOGRAPHY APPARATUS WITHOUT COUPLING ROD

[75] Inventors: Peter Biermann, Norderstedt; Wilfried Pfeiffer, Quickborn, both of Germany

[73] Assignee: U.S. Philips Corporation, New York, N.Y.

[21] Appl. No.: 08/966,598

[22] Filed: Nov. 10, 1997

[30] Foreign Application Priority Data

Nov. 15, 1996 [DE] Germany ............................ 196 47 243

[51] Int. Cl.[6] ............................................... A61B 6/08
[52] U.S. Cl. ............................................. 378/21; 378/206
[58] Field of Search ............................... 378/206, 21, 25, 378/26

[56] References Cited

U.S. PATENT DOCUMENTS 4,442,533  4/1984  Lescrenier ................................. 378/25

FOREIGN PATENT DOCUMENTS

0054798B1  6/1982  European Pat. Off. .

*Primary Examiner*—Craig E. Church
*Attorney, Agent, or Firm*—Dwight H. Renfrew, Jr.

[57] ABSTRACT

A method of and operation for controlling the motions of a radiation source (24) and a radiation detector, for example a film cassette (25), in relation to an adjusted slice position, for example a slice level (19), in a linear tomography apparatus without coupling rod, which tomography apparatus includes a table (10) for accommodating an object (18) to be imaged by tomography includes adjustment of a light indicator (17), adjustably mounted on the table (10), to the position of the slice in the object (18), measurement of data indicating the adjusted slice position, application of the measured slice position data to a system control unit (22), and adjustment of the source (24) and the radiation detector (25) in relation to the measured slice position (19) in conformity with the data applied.

11 Claims, 2 Drawing Sheets

METHOD OF CONTROLLING A TOMOGRAPHY APPARATUS WITHOUT COUPLING ROD

BACKGROUND OF THE INVENTION

1. Field of the Invention

The invention relates to a method of controlling the motions radiation source and a radiation detector, for example a film cassette, in relation to an adjusted slice position, for example a slice level, in a tomography apparatus without coupling rod, which tomography apparatus includes a table for accommodating an object, such as organ to be imaged by tomography. The invention also relates to a device for carrying out the method.

2. Description of the Related Art

Linear X-ray tomography of a slice or layer in a object has been performed for decades using a mechanically coupled source and film. Because of the recent introduction of (electronic) tomography without coupling rod, the mechanical pivot used thus far for mounting a light indicator for marking the adjusted slice position in the patient is no longer present. Since this location for mounting a light indicator no longer exists in electronic tomography, it is problematic for the X-ray technician to achieve exact adjustment of the position of the slice the patient.

EP 0 054 798 B1 discloses an adjusting unit for a radiation tomography apparatus. This construction includes a light beam detection device which is situated in line with a light beam generator, the horizontal line extending through the center of a region to be irradiated. The object to be irradiated is arranged on a height-adjustable table which is provided with a drive unit for raising and lowering. The data produced during the height adjustment of the table are electronically acquired and a control unit calculates a compare signal from the data acquired so as to store this signal for alignment of the horizontal line of the imaging region relative to the center of the part of the object to be imaged.

SUMMARY OF THE INVENTION

It is an object of the invention to provide a more simple and reliable method of the kind set forth.

This object is achieved according to the invention in that a light indicator which is adjustably mounted on the table is adjusted to the slice position of the organ to be imaged by tomography, the adjusted slice position is measured, the measured slice position data is supplied to a system control unit, and the source and the radiation detector are adjusted in conformity with the measured slice position in conformity with the data applied.

A method of this kind can be readily performed. The light indicator can be simply adjusted by hand. Furthermore, the slice position thus adjusted can be simply and quickly read from a scale and applied to the system control unit, for example by hand. The system control unit then provides the matched source and radiation detector motions required for this slice position. It is an advantageous aspect of this method that it does not require adjustment of the table. The measured data concerning the adjusted slice position is now applied to the system control unit which controls the necessary motions of the source and the radiation detector.

The slice position can be simply adjusted either by hand or by means of a motor. The radiation detector may also be, for example a flat digital detector.

A method in which the adjusted slice position is read from a scale and applied to the system control unit by hand can be quickly and simply carried out.

An attractive embodiment of the invention is a method in which an adjusted slice position is electrically measured and the measurement data is automatically acquired and applied to the system control unit. The amount of work required is thus minimized.

A device for carrying out the above method is characterized in that it includes a holder which accommodates a built-in adjustable slider and is mounted on the table in the vicinity of the organ to be imaged, a light indicator which is mounted on the slider, means for the acquisition of the slice position data, and a system control unit for processing the slice position data and for applying the data to an apparatus for controlling the motions of the source and the radiation detector.

Using few components, such a device enables reliable, fast marking of the adjusted slice position on the patient and also provides corresponding alignment of the radiation source and the radiation detector.

Attractive marking is achieved when the light indicator is formed by a laser light indicator.

The inclusion of an electronic device for measuring the instantaneously adjusted slice position enables fast input of the data when the data is read from the scale by the technician.

A simplified embodiment is characterized in that it includes a device for the automatic acquisition and input of the electronically measured slice position data.

In a further embodiment of the invention the holder can be mounted in such a manner that it can be removed or swung aside. Thus, the working area of the table is not interfered with when the slice position need not be adjusted.

For electronic measurement, acquisition and application of the slice position data in an embodiment of the invention, signal transmission takes place either via a cable or in a wireless manner, for example by radio or ultrasound.

A simple embodiment of the invention is characterized in that it includes a battery for power supply of the light indicator mounted in the holder.

BRIEF DESCRIPTION OF THE DRAWING

The FIGS. 1 and 2 of the drawing show an embodiment of the subject matter of the invention, wherein.

DETAILED DESCRIPTION OF THE PREFERRED EMBODIMENTS

Figure 1:
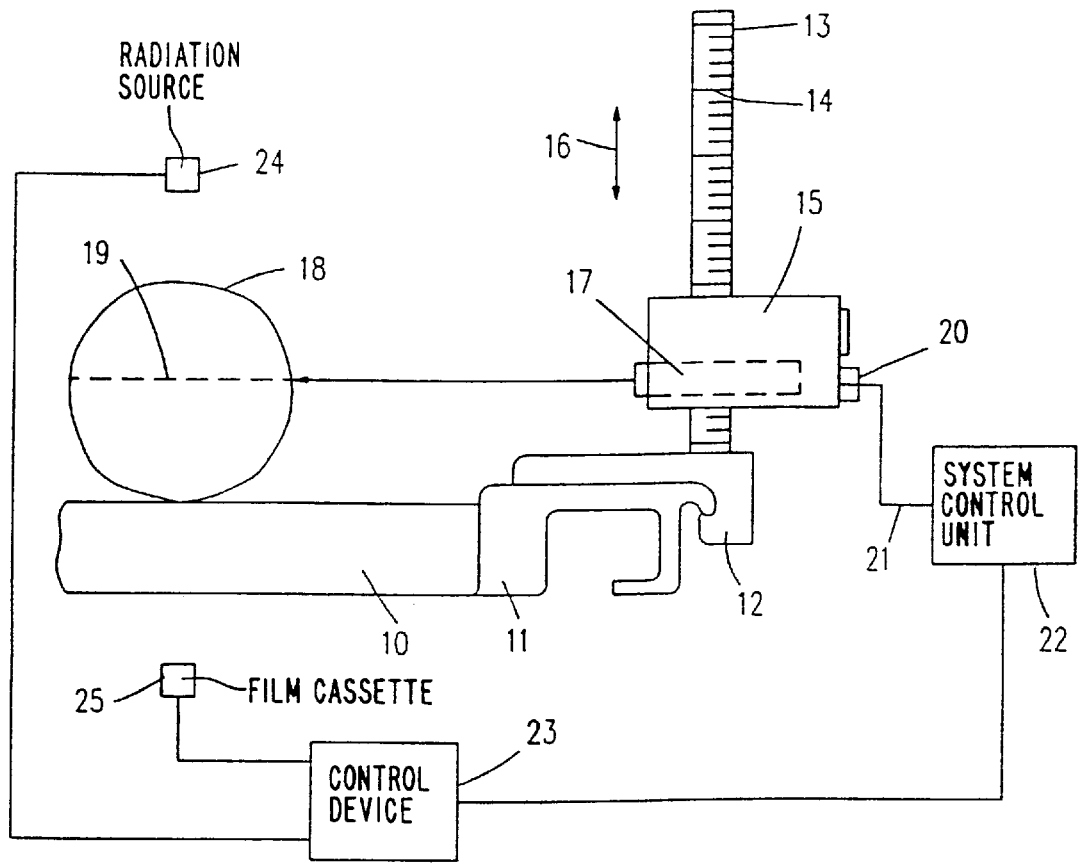
FIG. 1 shows a part of a table with a holder provided with a laser indicator.

FIG. 1 shows a part of a table 10 of a tomography apparatus with a holder 12 which is detachably secured in an edge profile 11 of the table. The holder 12 includes a strip 13 on which a scale 14 is provided. A slider 15 is mounted on the strip 13 so as to be vertically movable in the direction 16. The slider 15 supports a laser light indicator 17 for adjusting a given slice level 19 in an object 18 on the table 10. The slider 15 can be adjusted on the strip 13 either by hand or by means of a motor. The slice level 19 adjusted by means of the slider 15 can be read from the scale 14 as shown in FIG. 1. In the embodiment shown in FIG. 1 the data read can be applied to a control grip 20 by hand, after which it is applied to a system control unit 22 via a cable 21. The system control unit 22 communicates with a control device 23 which aligns, on the basis of the data received, a radiation source 24 and a radiation detector in the form of a film cassette 25 in relation to the adjusted slice level 19.

Figure 2:
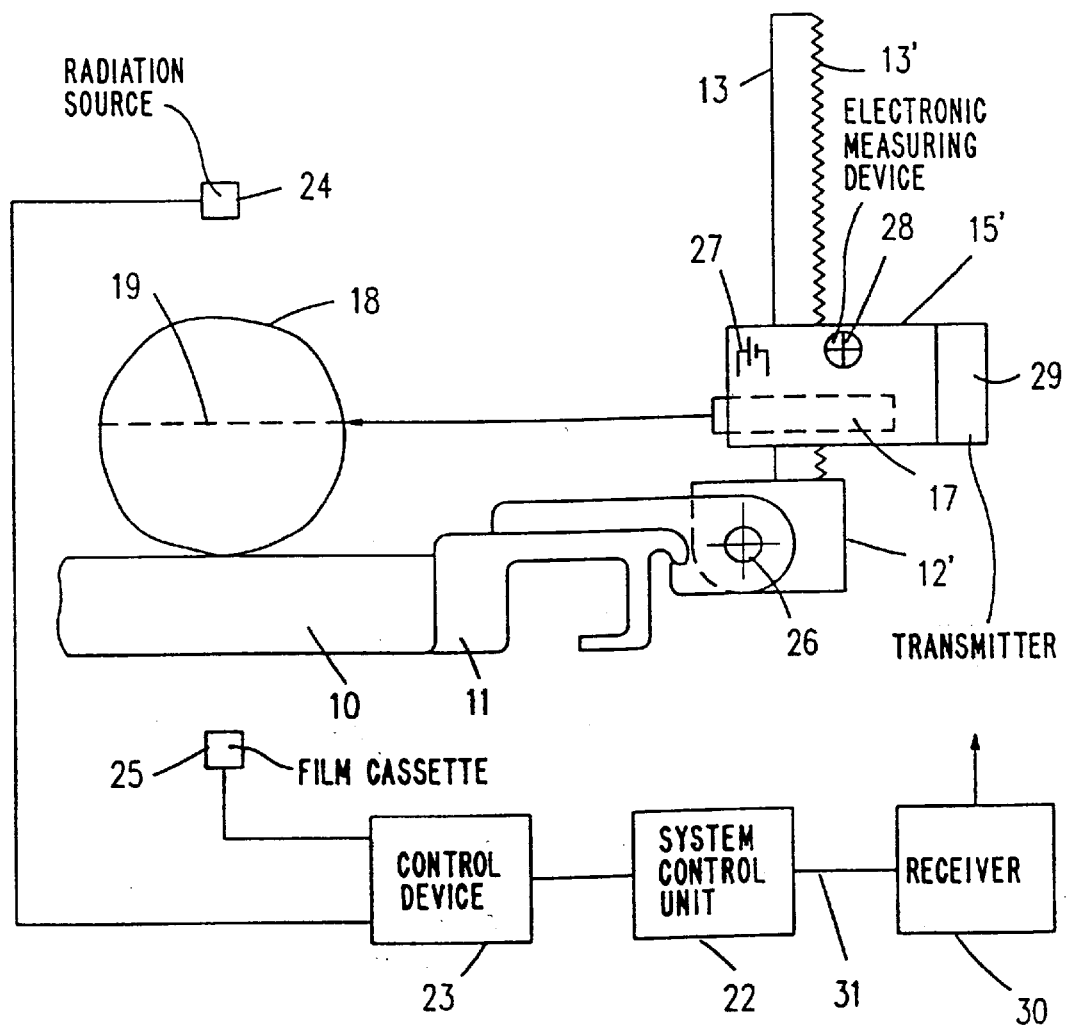
FIG. 2 shows a special embodiment of the laser indicator in a slightly modified holder.

FIG. 2 shows a holder 12' which can be swung away laterally about the pivot 26. This embodiment also includes a slider 15' which is provided with a battery 27 for power supply of the light indicator. The reference numeral 28 denotes an electronic measuring device for electronic measurement of the adjusted level. The electronically acquired measurement data are now applied to a receiver 30 in a wireless manner, via a transmitter 29 accommodated in the slider 15'; the receiver applies the corresponding level data to the system control unit 22 via a cable 31. The data is then applied to the control device 23 for controlling the source 24 and the film cassette 25. The reference numeral 13' denotes a toothed rack.

We claim:

1. A method of controlling the movements of a radiation source and a radiation detector in relation to an adjusted slice position in a tomography apparatus which does not include a mechanical coupling rod between the radiation source and detector but which includes a table for accommodating an object to be imaged by tomography, said method comprising:

adjusting a light indicator which is adjustably mounted on the table to the position of the slice in the object to be imaged by tomography, measuring data indicative of the adjusted slice position, supplying the measured slice position data to a system control unit, and causing the system control unit to electrically adjust the positions of the radiation source and the radiation detector in conformity with the measured slice position data.

2. A method as claimed in claim 1, wherein data indicating the adjusted slice position is read from a scale and applied to the system control unit by hand.

3. A method as claimed in claim 1, wherein data indicating the adjusted slice position is electronically measured and automatically acquired and supplied to the system control unit.

4. A device for controlling the movements of a radiation source and a radiation detector in relation to an adjusted slice position in a tomography apparatus which does not include a mechanical coupling rod between the radiation source and detector but which includes a table for accommodating an object to be imaged by tomography; said device comprising:

a holder which accommodates a built-in adjustable slider and is mounted on the table in the vicinity of the object to be imaged, a light indicator which is mounted on the slider, means for acquisition of slice position data, and a system control unit for processing the slice position data and for supplying the processed data to an apparatus for electrically controlling movement of the source and the radiation detector in conformity with the processed data.

5. A device as claimed in claim 4, wherein the radiation source is a laser and the light indicator is a laser light indicator.

6. A device as claimed in claim 4, further comprising an electronic device for measuring the instantaneously adjusted slice position.

7. A device as claimed in claim 4, further comprising a control grip for applying the slice position data read from a scale to the system control unit by hand.

8. A device as claimed in claim 4, wherein the means for acquisition of slice position data is an electronic device for automatically acquiring and supplying said data to the system control unit.

9. A device as claimed in claim 4, wherein the holder is constructed so that it can be removed or swung aside.

10. A device as claimed in claim 8, wherein automatic acquisition and supply of the slice position data to the system control unit takes place either via a cable or by wireless transmission.

11. A device as claimed in claim 5, wherein the slider accommodates a battery for power supply of the laser light indicator.

* * * * *